United States Patent
Wingert et al.

(10) Patent No.: US 12,128,157 B2
(45) Date of Patent: Oct. 29, 2024

(54) ABSORBENT ARTICLES INCLUDING HIPE FOAM ENHANCED WITH CLAY NANOPLATELETS, AND METHOD OF MANUFACTURE

(71) Applicant: The Procter & Gamble Company, Cincinnati, OH (US)

(72) Inventors: Maxwell Joseph Wingert, Liberty Township, OH (US); Josef Breu, Bayreuth (DE); Lina Mayr, Bayreuth (DE); Steven Ray Merrigan, West Chester, OH (US); Arsen Arsenov Simonyan, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 728 days.

(21) Appl. No.: 17/358,041

(22) Filed: Jun. 25, 2021

(65) Prior Publication Data
US 2021/0402066 A1 Dec. 30, 2021

Related U.S. Application Data

(60) Provisional application No. 63/044,432, filed on Jun. 26, 2020.

(51) Int. Cl.
| | |
|---|---|
| A61L 27/56 | (2006.01) |
| A61F 13/472 | (2006.01) |
| A61F 13/535 | (2006.01) |
| A61L 15/18 | (2006.01) |
| A61L 15/42 | (2006.01) |
| A61L 27/04 | (2006.01) |
| A61L 27/16 | (2006.01) |
| A61F 13/53 | (2006.01) |

(52) U.S. Cl.
CPC ............ *A61L 27/56* (2013.01); *A61F 13/472* (2013.01); *A61F 13/535* (2013.01); *A61L 15/18* (2013.01); *A61L 15/425* (2013.01); *A61L 27/047* (2013.01); *A61L 27/16* (2013.01); *A61F 2013/530817* (2013.01); *A61L 2400/12* (2013.01)

(58) Field of Classification Search
CPC .............................. A61F 13/472; A61L 27/56
See application file for complete search history.

(56) References Cited

U.S. PATENT DOCUMENTS

| | | | | |
|---|---|---|---|---|
| 5,633,291 A | * | 5/1997 | Dyer ................... | C08J 9/283 521/64 |
| 5,795,921 A | | 8/1998 | Dyer et al. | |
| 5,900,437 A | * | 5/1999 | Mitchell .................. | C08J 9/28 521/64 |
| 8,785,079 B1 | * | 7/2014 | Gross ................... | H01M 4/661 429/534 |
| 2004/0158214 A1 | | 8/2004 | Ponomarenko et al. | |
| 2012/0157622 A1 | * | 6/2012 | Lindner ................. | C09C 1/42 524/790 |
| 2015/0335498 A1 | | 11/2015 | Hubbard, Jr. et al. | |
| 2015/0374560 A1 | * | 12/2015 | Hubbard, Jr. ........... | A61L 15/60 428/316.6 |
| 2020/0253793 A1 | | 8/2020 | Rawat | |

FOREIGN PATENT DOCUMENTS

| | | |
|---|---|---|
| CN | 104558438 A | 4/2015 |
| CN | 106456824 A | 2/2017 |

OTHER PUBLICATIONS

PCT Search Report and Written Opinion for PCT/US2021 /039018 dated Oct. 12, 2021, 12 pages.
Ahmed M. Serry et al: "Effect of nanoclay on the microcellular structure and morphology of high internal phase emulsion (HIPE) foams",Asia-Pacific Journal of Chemical Engineering, vol. 4, No. 2, Mar. 1, 2009 (Mar. 1, 2009), pp. 120-124, XP055846754, usISSN: 1932-2135, DOI: 10.1002/apj.218p. 120-p. 123.
Mert Hatice Hande et al: "Adsorptive polyHIPE composites based on biosorbent immobilized nanoclay: Effects ofimmobilization techniques",Polymer Engineering and Science, [Online]vol. 58, No. 8, Aug. 1, 2017 (Aug. 1, 2017)' pp. 1229-1240, XP055846473, ISSN: 0032-3888, DOI: 10.1002Retrieved from the Internet:URL: https://api.wiley.com/onlinelibrary/tdm/vl/articles/10.1002/pen. 24684.
Lina Mayr, et al., "Structural and mechanical impact of synthetic clay in composite foams made via high-internal phase emulsions", Polymer Composites, vol. 42, No. 1, pp. 353-361, Oct. 24, 2020.
Wu Tongfei, et al., "Evaluation of ammonium terminated PMMA as compatibilizers for monomer casting polyamide6/ clay nanocomposites", Journal of Polymer Science: Part B: Polymer Physics, vol. 46, No. 17, pp. 1802-1810, Sep. 1, 2008.

\* cited by examiner

*Primary Examiner* — Irina Krylova
(74) *Attorney, Agent, or Firm* — Amanda Herman Berghauer; William E. Gallagher

(57) ABSTRACT

Open-cell foam having a structure of interconnected struts formed of polymeric material and defining open cells, resulting from polymerization of a continuous phase of a high internal phase water-in-oil emulsion, the struts comprising the polymeric material with clay nanoparticles at least partially captured therewithin, is disclosed. The clay nanoparticles may be present in combination with a surface modifier. Methods for making the open-cell foam are also disclosed. Absorbent articles including the open cell foam are also disclosed.

7 Claims, 7 Drawing Sheets

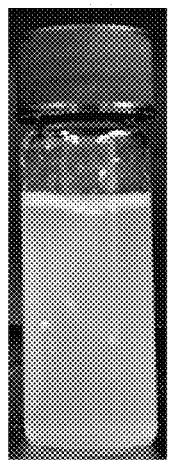 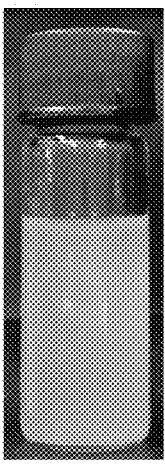 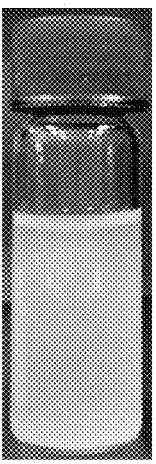   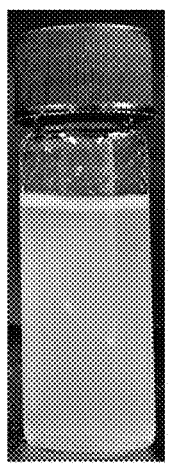 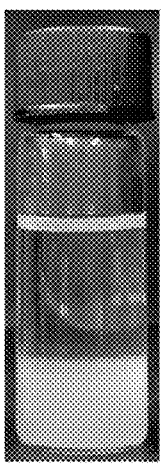 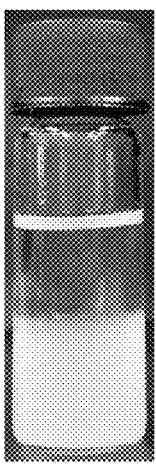
FIG. 3A  FIG. 3B  FIG. 3C    FIG. 4A  FIG. 4B  FIG. 4C
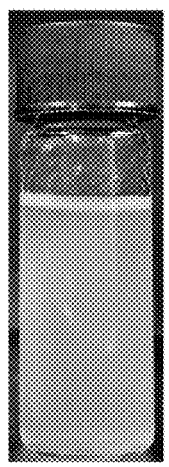 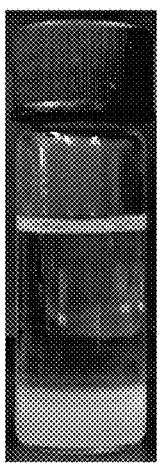 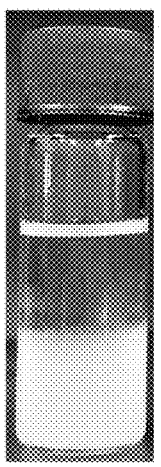   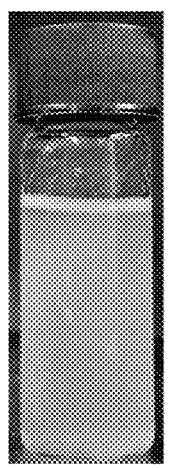 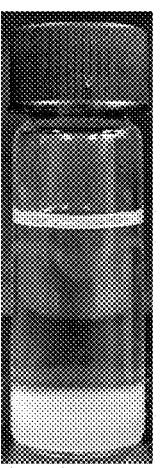 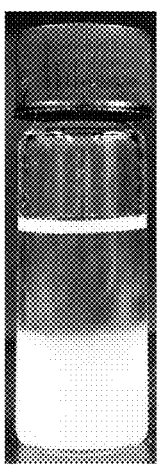
FIG. 5A  FIG. 5B  FIG. 5C    FIG. 6A  FIG. 6B  FIG. 6C

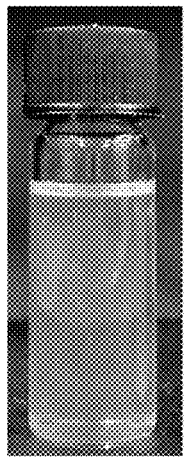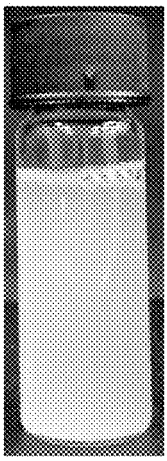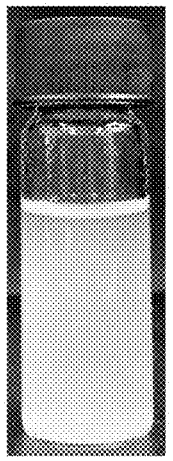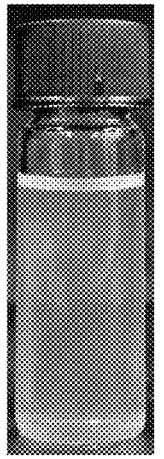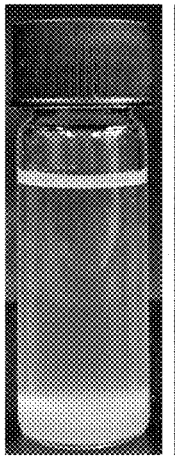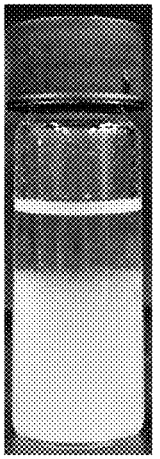
FIG. 7A   FIG. 7B   FIG. 7C          FIG. 8A   FIG. 8B   FIG. 8C
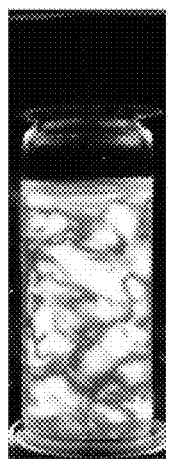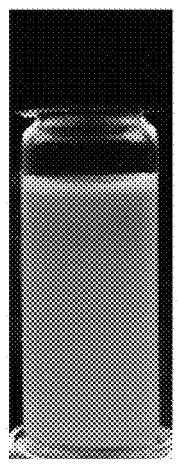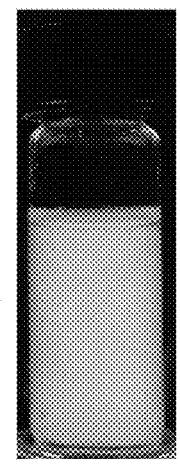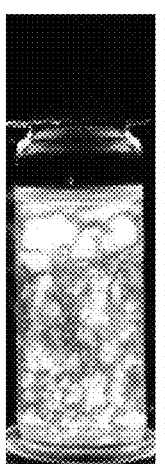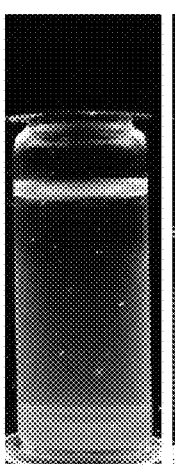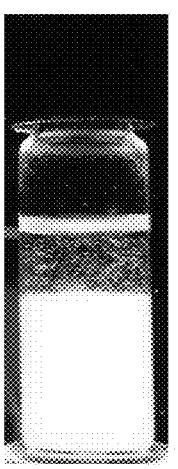
FIG. 9A   FIG. 9B   FIG. 9C          FIG. 10A   FIG. 10B   FIG. 10C

ABSORBENT ARTICLES INCLUDING HIPE FOAM ENHANCED WITH CLAY NANOPLATELETS, AND METHOD OF MANUFACTURE

CROSS REFERENCE TO RELATED APPLICATION

This application claims the benefit of U.S. Provisional Application No. 63/044,432, filed Jun. 26, 2020, the substance of which is incorporated herein by reference.

BACKGROUND

An important component of disposable absorbent articles such as feminine hygiene pads, incontinence pads and pants, diapers and training pants is the absorbent core structure. Absorbent foams having open-cell structures, resulting from polymerization of monomers included in the continuous oil phase of a high internal phase water-in-oil emulsion (HIPE), have been produced for commercial use for a number of years. Examples include foams produced by The Procter & Gamble Company, Cincinnati, Ohio, for use as absorbent components of feminine hygiene pads. Useful polymer foams include those having structures formed of material polymerized from continuous oil phases of HIPEs that are predominately acrylate and/or methacrylate type monomers, known as (meth)acrylate(s).

These foams can be manufactured to be highly absorbent, flexible and have a resilient, cushiony feel, making them well-suited to the uses made of them. However, any improvements that might be identified and successfully incorporated into the foam product and/or its manufacturing process, including improvements that reduce material and/or manufacturing costs; enhance mechanical properties of the foam product; enhance absorbency performance of the foam product, etc., would provide competitive advantages to the manufacturer.

In recent years exploration has been made into incorporation of clay into a foam structure, to improve one or more of these attributes. The properties of various clays hold promise for enhancing desirable attributes of absorbent HIPE foams.

In order to incorporate clay particles into the polymer material forming the foam structure (in contrast with merely depositing clay particles on surfaces of the structure after polymerization), it is likely more effective to immerse, disperse and suspend the clay particles within the monomer oil phase, rather than blending the clay particles into the aqueous phase or the aqueous phase/oil phase combination, prior to emulsification and polymerization of the oil phase. Because clays are ordinarily naturally hydrophilic, however, they resist immersion in oil phase materials used to make HIPE foams suitable for uses contemplated herein.

For this reason, to effect such immersion, substantial (costly) mechanical energy input is required to agitate the foam precursor liquid(s) to disperse clay particles into an oil phase material blend, either prior to or during the emulsion-making process.

As an alternative and/or supplementary measure to input of large amounts of mechanical energy, the clay particles may be provided with an applied surface modification agent that renders their surfaces organophilic, i.e., compatible with the oil phase component blend. Surface modification agents identified to date, however, have not been particularly effective at facilitating good clay particle dispersion, emulsion stability, and avoidance of clay particle agglomeration and sedimentation, all of which affect one's ability to manufacture a foam with desirable attributes. To date, efforts to incorporate clays into HIPEs have been unsuccessful in achieving good dispersion of clay particles throughout the oil phase, emulsion stability, and improvements to properties of foam structures formed of materials polymerized from the monomer oil phases of water-in-oil HIPEs.

BRIEF DESCRIPTION OF THE DRAWINGS

FIG. 3A is a photograph of a glass vial containing approximately 3 mL of an emulsifier-containing oil phase blend including 1 weight percent HecPEHMA, taken approximately 2 minutes following pouring of the blend into the vial.

FIG. 3B is a photograph of a glass vial containing approximately 3 mL of an emulsifier-containing oil phase blend including 1 weight percent organophilized Montmorillonite, taken approximately 2 minutes following pouring of the blend into the vial.

FIG. 3C is a photograph of a glass vial containing approximately 3 mL of an emulsifier-containing oil phase blend including 1 weight percent HecCTAB, taken approximately 2 minutes following pouring of the blend into the vial.

FIG. 4A is a photograph of the vial shown in FIG. 3A, taken 1 hour following pouring of the blend into the vial.

FIG. 4B is a photograph of the vial shown in FIG. 3B, taken 1 hour following pouring of the blend into the vial.

FIG. 4C is a photograph of the vial shown in FIG. 3C, taken 1 hour following pouring of the blend into the vial.

FIG. 5A is a photograph of the vial shown in FIG. 3A, taken 24 hours following pouring of the blend into the vial.

FIG. 5B is a photograph of the vial shown in FIG. 3B, taken 24 hours following pouring of the blend into the vial.

FIG. 5C is a photograph of the vial shown in FIG. 3C, taken 24 hours following pouring of the blend into the vial.

FIG. 6A is a photograph of the vial shown in FIG. 3A, taken 1 week following pouring of the blend into the vial.

FIG. 6B is a photograph of the vial shown in FIG. 3B, taken 1 week following pouring of the blend into the vial.

FIG. 6C is a photograph of the vial shown in FIG. 3C, taken 1 week following pouring of the blend into the vial.

FIG. 7A is a standard-lighting photograph of a glass vial containing approximately 3 mL of an emulsifier-free oil phase blend including 1 weight percent HecPEHMA, taken approximately 2 minutes following pouring of the blend into the vial.

FIG. 7B is a standard-lighting photograph of a glass vial containing approximately 3 mL of an emulsifier-free oil phase blend including 1 weight percent organophilized Montmorillonite, taken approximately 2 minutes following pouring of the blend into the vial.

FIG. 7C is a standard-lighting photograph of a glass vial containing approximately 3 mL of an emulsifier-free oil phase blend including 1 weight percent HecCTAB, taken approximately 2 minutes following pouring of the blend into the vial.

FIG. 8A is a standard-lighting photograph of the vial shown in FIG. 7A, taken 24 hours following pouring of the blend into the vial.

FIG. 8B is a standard-lighting photograph of the vial shown in FIG. 7B, taken 24 hours following pouring of the blend into the vial.

FIG. 8C is a standard-lighting photograph of the vial shown in FIG. 7C, taken 24 hours following pouring of the blend into the vial.

FIG. 9A is a polarized-lighting photograph of the vial shown in FIG. 7A, taken approximately 2 minutes following pouring of the blend into the vial.

FIG. 9B is a polarized-lighting photograph of the vial shown in FIG. 7B, taken approximately 2 minutes following pouring of the blend into the vial.

FIG. 9C is a polarized-lighting photograph of the vial shown in FIG. 7C, taken approximately 2 minutes following pouring of the blend into the vial.

FIG. 10A is a polarized-lighting photograph of the vial shown in FIG. 7A, taken 24 hours following pouring of the blend into the vial.

FIG. 10B is a polarized-lighting photograph of the vial shown in FIG. 7B, taken 24 hours following pouring of the blend into the vial.

FIG. 10C is a polarized-lighting photograph of the vial shown in FIG. 7C, taken 24 hours following pouring of the blend into the vial.

DEFINITIONS

With respect to a feminine hygiene pad that is opened and laid out flat on a horizontal planar surface, "lateral" refers to a direction perpendicular to the longitudinal direction and parallel the horizontal planar surface.

With respect to a feminine hygiene pad that is opened and laid out flat on a horizontal planar surface and having a length measured from forward end to rearward end, "longitudinal" refers to a direction parallel with the line along which the length is measured, and parallel to the horizontal planar surface. "Length" refers to a dimension measured in the longitudinal direction.

With respect to a feminine hygiene pad, the terms "front," "rear," "forward" and "rearward" relate to features or regions of the pad corresponding to the position it would occupy as ordinarily worn by a user, and the front and rear of the user's body when standing.

With respect to a feminine hygiene pad that is opened and laid out flat on a horizontal planar surface, or a nonwoven web material laid out flat on a horizontal planar surface, "z-direction" refers to a direction perpendicular to the horizontal planar surface, and any plane parallel to the horizontal planar surface may be referred to as an "x-y plane". When the pad is being worn by a user (and thus has been urged into a curving configuration), "z-direction" at any particular point location on the pad refers to a direction normal to the wearer-facing surface of the pad at the particular point location. With respect to a nonwoven web during its manufacture, "z-direction" refers to a direction orthogonal to both the machine direction and the cross direction of manufacture, and any plane parallel to the machine direction and cross direction may be referred to as an "x-y plane".

With respect to a feminine hygiene pad, "wearer-facing" is a relative locational term referring to a feature of a component or structure of the pad that when in use that lies closer to the wearer than another feature of the component or structure that lies along the same z-direction. For example, a topsheet has a wearer-facing surface that lies closer to the wearer than the opposite, outward-facing surface of the topsheet.

With respect to a feminine hygiene pad, "outward-facing" is a relative locational term referring to a feature of a component or structure of the pad that when in use that lies farther from the wearer than another feature of the component or structure that lies along the same z-direction. For example, a topsheet has an outward-facing surface that lies farther from the wearer than the opposite, wearer-facing surface of the topsheet.

DESCRIPTION

Figure 1:
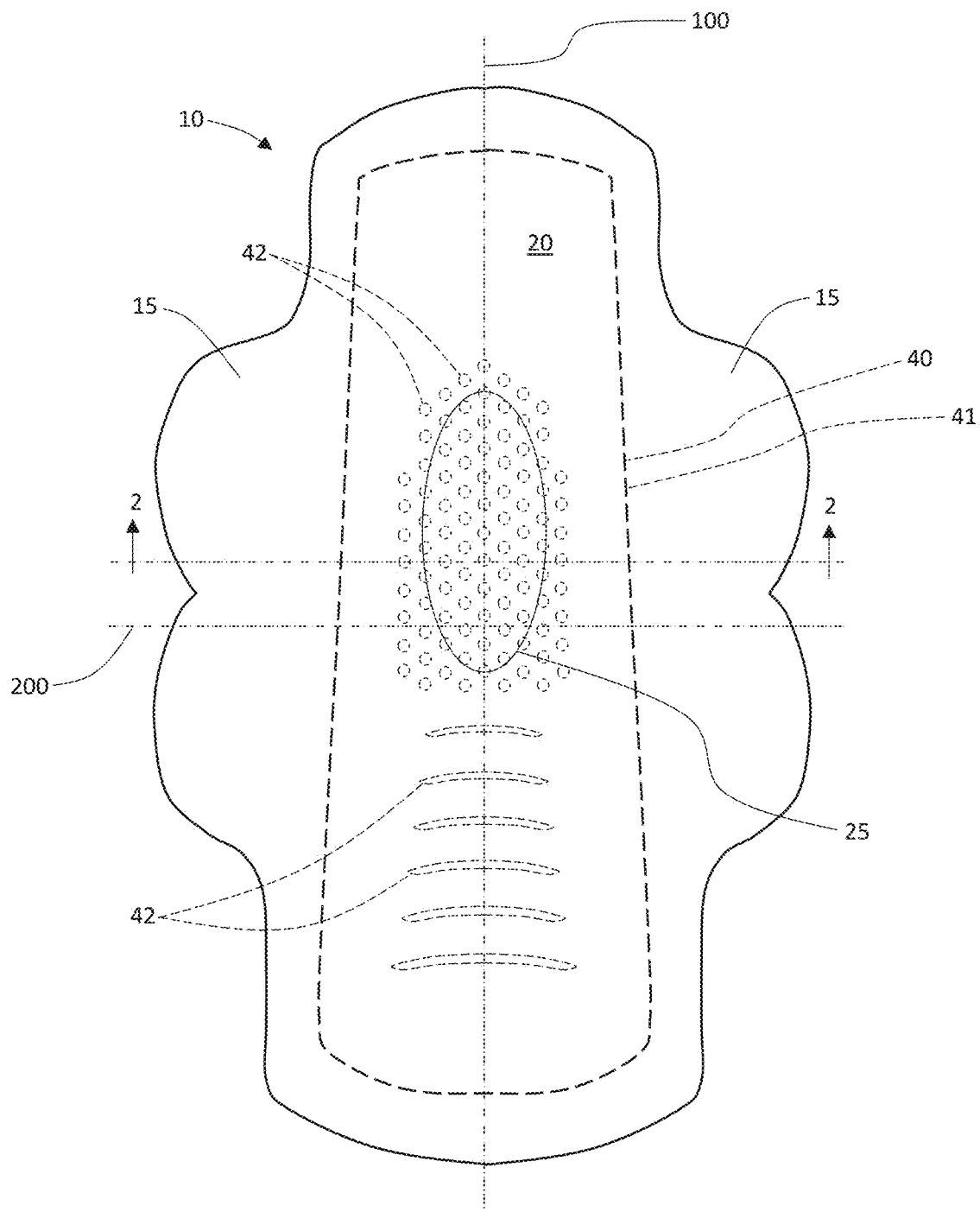
FIG. 1 is a plan view of a feminine hygiene pad, topsheet side facing the viewer.
Figure 2A:
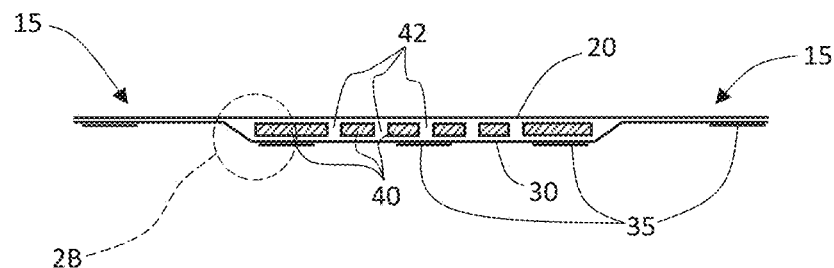
FIG. 2A is a schematic lateral cross section of the feminine hygiene pad of FIG. 1.

Referring to FIGS. 1 and 2A, a feminine hygiene pad 10 may include a liquid permeable topsheet 20, a liquid impermeable backsheet 30 and an absorbent layer 40 disposed between the topsheet and the backsheet. The absorbent layer has an outer perimeter 41. In regions outside the outer perimeter 41, the topsheet and the backsheet may be bonded together in laminated fashion by any suitable mechanism including but not limited to adhesive bonding, thermal bonding, pressure bonding, etc., thereby retaining and holding the absorbent layer 40 in place between the topsheet 20 and the backsheet 30. Pad 10 may include opposing wing portions 15 extending laterally outside of perimeter 41 by a comparatively greater width dimension than the main portion of the pad. The outer surface of the backsheet forming the undersides of the main portion and the wing portions may have deposits of adhesive 35 thereon. Adhesive deposits 35 may be provided to enable the user to adhere the pad to the inside of her underpants in the crotch region thereof, and wrap the wing portions through and around the inside edges of the leg openings of the underpants and adhere them to the outside/underside of the underpants in the crotch region, providing supplemental holding support and helping guard the leg edges of the underpants against soiling. When pad 10 is packaged, adhesive deposits 35 may be covered by one or more sheets of release film or paper (not shown) that covers/shields the adhesive deposits 35 from contact with other surfaces until the user is ready to remove the release film or paper and place the pad for use.

Topsheet

Topsheet 20 may be formed of any suitable hydrophilic nonwoven web material. Referring back to the figures, the topsheet 20 is positioned adjacent a wearer-facing surface of the absorbent layer 40 and may be joined thereto and to the backsheet 30 by any suitable attachment or bonding method. The topsheet 20 and the backsheet 30 may be joined directly to each other in the peripheral regions outside the perimeter 41 of the absorbent layer 40 and may be indirectly joined by directly joining them respectively to wearer-facing and outward-facing surfaces of the absorbent layer or additional optional layers included with the pad.

The pad 10 may have any known or otherwise effective topsheet, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. A suitable topsheet may be made of various materials such as woven and nonwoven web materials.

Nonlimiting examples of nonwoven web materials that may be suitable for use as the topsheet include fibrous materials made from natural fibers, modified natural fibers, synthetic fibers, or combinations thereof. Some suitable examples are described in U.S. Pat. Nos. 4,950,264, 4,988, 344; 4,988,345; 3,978,185; 7,785,690; 7,838,099; 5,792, 404; and 5,665,452.

In some examples, the topsheet may include tufts as described in U.S. Pat. Nos. 8,728,049; 7,553,532; 7,172, 801; 8,440,286; 7,648,752; and 7,410,683. The topsheet may have a pattern of discrete hair-like fibrils as described in U.S. Pat. No. 7,655,176 or 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651.

As contemplated herein, component nonwoven web material from which topsheet 20 may be cut may be a nonwoven web material that includes or consists predominately (by weight) or entirely of cellulosic plant fibers such as fibers of cotton, flax, hemp, jute or mixtures thereof, that are either naturally hydrophilic or suitably processed so as be rendered hydrophilic (or have increased hydrophilicity), and processed to be suitably soft-feeling against the skin. Plant-based fibers may be preferred, to appeal to consumer preferences for natural products. In other examples, semisynthetic fibers derived from cellulosic material, such as rayon (including viscose, lyocell, MODAL (a product of Lenzing AG, Lenzing, Austria) and cuprammonium rayon) may be used.

The nonwoven web may be formed via any suitable process by which fibers of finite lengths may be distributed and accumulated in a controlled fashion onto a forming belt to form a batt having a desired distribution of fibers, to a desired basis weight. Suitable processes may include carding, airlaying and wetlaying. The batt may be processed to consolidate the fibers and entangle them in the z-direction, by processes that may include calendering, needlepunching and hydroentanglement via water jets.

In some examples a topsheet cut from a nonwoven including or consisting predominately (by weight) or entirely of plant fibers, such as cotton fibers, may be preferred. In some examples, the nonwoven web material may be formed via a carding process. In other examples, the nonwoven web material may be formed via an airlaying or wetlaying process. In still other examples the nonwoven web material may be formed in a co-forming process in which plant-based fibers of finite lengths are physically blended or mixed with streams of spun fibers of longer but indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

In order to ensure that fluid contacting the top (wearer-facing) surface of a hydrophilic topsheet will move suitably rapidly via capillary action in a z-direction to the bottom (outward-facing) surface of the topsheet where it can be drawn into the absorbent layer, it may be important to ensure that the nonwoven web material forming the topsheet has an appropriate weight/volume density, reflecting suitable presence of interstitial passageways among and between the constituent fibers, through which fluid may move within the nonwoven material. A nonwoven with fibers that are consolidated too densely will have insufficient numbers and volume of interstitial passageways, and the nonwoven will obstruct rather than facilitate rapid z-direction fluid movement. On the other hand, a nonwoven with fibers that are not consolidated enough to provide sufficient fiber-to-fiber contact and/or sufficiently small interstitial passageways may provide insufficient potential for wicking in the z-direction via capillary action. In examples in which the nonwoven web material includes or consists predominately or entirely of cotton fibers, for purposes of balancing priorities of absorbed fluid concealment and mechanical strength (needed for processing), versus limiting the quantity of topsheet material through which liquid must move in the z-direction to reach the absorbent layer beneath, it may be desired that the web have a basis weight of 20 gsm (herein, "gsm" means grams/m$^2$) to 50 gsm, more preferably 25 gsm to 45 gsm, and even more preferably 30 gsm to 40 gsm. In conjunction, it may be desired that the web have a density of 74 kg/m$^3$ to 110 kg/m$^3$ and more preferably 83 kg/m$^3$ to 101 kg/m$^3$, where density is calculated as basis weight divided by caliper (z-direction thickness, measured using the caliper measurement method set forth below). Alternatively, or in combination with control of the values above, the caliper of the topsheet material may be controlled, to balance competing needs for opacity and loft (which call for a higher caliper) vs. a limitation on the z-direction distance that discharged fluid must travel through the topsheet from the wearer-facing surface to the outward-facing surface, to reach the absorbent layer below. Thus, it may be desired that the manufacture of the topsheet material be controlled to produce a topsheet material having a caliper of 0.20 mm to 0.60 mm, more preferably 0.25 mm to 0.55 mm, and even more preferably 0.30 mm to 0.45 mm. For purposes herein, caliper is measured using the caliper measurement method set forth below.

Immediately following separation from the bolls, cotton fiber is naturally hydrophobic due to the presence of natural waxy and oily compounds on the surfaces of the fibers. After ginning to separate the cotton fiber from the seeds, masses of raw cotton fiber (stored and transported in bales) typically include substantial quantities of impurities (particulates, bits of plant matter, etc.), trapped within the fibrous matrices and/or adhered to the waxes and oils, that both discolor the cotton fiber and make it unsuitable for many uses. In order to make raw cotton fiber commercially acceptable for most uses, the fiber must first be processed in several steps to remove the impurities. Typical processes also remove the natural waxes and oils and render the cotton fiber hydrophilic. Hydrophobizing agents such as oils, waxes or silicones can be reintroduced to render the cotton fibers and cotton-based fibrous structure hydrophobic and nonabsorbent, but for purposes herein an unapertured hydrophobic cotton-based topsheet would be unsuitable because it would not suitably accept and wick a discharge of fluid.

Following processing to remove impurities a mass of cotton fiber will be further mechanically processed to convert it to its intended end use condition and structure. Due to its hydrophilic nature, any mass of processed cotton fiber—whether appearing as a component of a textile/cloth, a paper product, a nonwoven web product or an absorbent product, will be absorbent of aqueous fluid to some extent, and will exhibit capillary wicking properties.

Rayon (including viscose, lyocell, tencel, cuprammonium rayon, etc.) fiber is manufactured from regenerated cellulose. At a molecular level, it is chemically similar to cotton fiber. At the fiber level rayon fiber can be imparted with complex surface geometry and substantial curl or crimp, and is naturally hydrophilic. Masses of rayon fiber typically have absorbency properties exceeding those of masses of cotton fiber.

Absorbency and wicking performance may vary according to, and may be manipulated by, the manner in which the fiber is further processed. Factors such as level of consolidation (i.e., densification) of the fiber mass in the end structure and orientations of the individual fibers within the end structure can affect absorbency and wicking performance.

Thus, for purposes contemplated herein, in combination with being imparted with a suitable basis weight, density and/or caliper as discussed above, it may be desired that a cotton- and/or rayon-based nonwoven web used to make the topsheet be formed via a nonwoven web manufacturing process in which substantial numbers of the fibers are imparted with directional orientation that includes some z-direction orientation, rather than orientations predominately biased along the machine direction or x-y plane of formation of the web structure. Following any suitable processes in which fibers are distributed and laid down in a batt on a horizontal forming belt (e.g., airlaying, wetlaying, carding, etc.), additional process steps that forcibly reorient some of the fibers or portions thereof in the z-direction may be employed. Suitable process steps may include needlepunching and hydroentangling. Hydroentangling, in which an array of fine, high-velocity water jets are directed at the batt as it is conveyed past them on a foraminous belt or drum, may be desired for its effectiveness in reorienting fibers while breaking fewer fibers and creating less broken fiber lint and surface fuzz (free fiber ends extending from the main structure of the web). A vacuum water removal system (in which air is drawn through the web in a z-direction into and through a pattern of orifices or pores on a drum or belt conveying the batt, pulling the hydrojetted water with it) may be desired because it tends to create, add, open and/or clear small z-direction passageways within the fiber matrix of the web, approximately in the pattern of the orifices or pores. Without intending to be bound by theory, it is believed that an increased number of fibers (or portions thereof) oriented in the z-direction, and the z-direction passageways, increase the ability and tendency of the web to wick aqueous fluid in the z-direction. In a topsheet, this would mean that the material can more readily wick aqueous fluid from the wearer-facing surface of the topsheet to the outward-facing surface of the topsheet, i.e., directly down to the absorbent layer below, and may thereby wick fluid less along x-y planar directions (causing a stain from discharged fluid to spread laterally and/or longitudinally).

Absorbent Layer

Figure 2B:
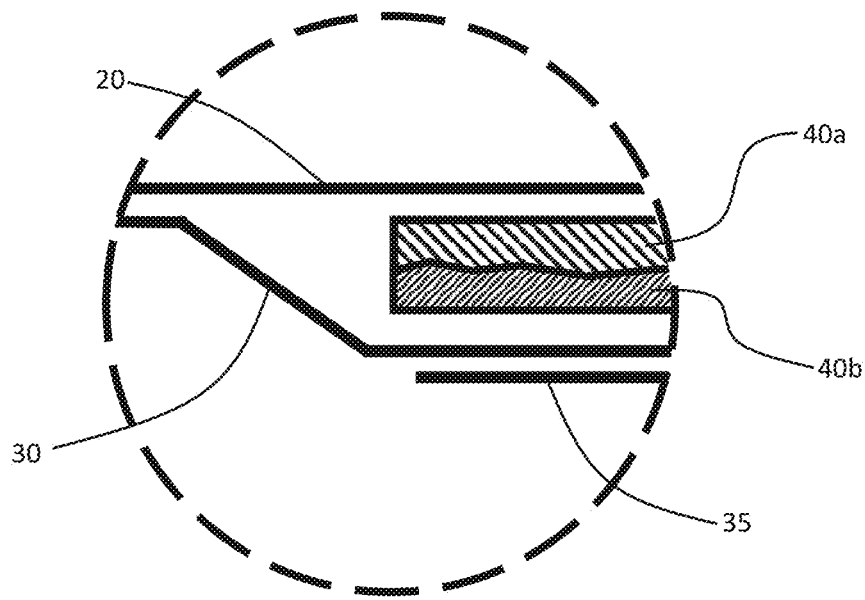
FIG. 2B is an enlarged portion 2B of the drawing of FIG. 2A, enlarged to depict sublayers of an absorbent layer.

In some examples the absorbent layer 40 may be formed of or include a layer of absorbent open-celled foam material. In some examples, the foam material may include at least first and second sublayers 40a, 40b (FIG. 2B) of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below.

The open-celled foam material may be a foam material that is manufactured via polymerization of the continuous oil phase of a water-in-oil high internal phase emulsion ("HIPE"). A HIPE for purposes herein is a two-phase water-in-oil emulsion in which the water-to-oil ratio is greater than about 2.85:1, i.e., about 74 percent aqueous/dispersed phase (by volume). Due to this relatively high ratio, upon emulsification sufficient to result in a foam of the type contemplated herein (i.e., average cell size 1 to 300 micrometers), the dispersed aqueous phase will have the form of droplets forced into polyhedral forms as a result of close crowding, separated by thin film walls formed of the oil/continuous phase.

The continuous oil phase includes monomers to be polymerized, and an emulsifier to help stabilize the HIPE. The oil phase may also include one or more photoinitiators. The monomer component may be included in an amount of from about 80% to about 99%, and in certain examples from about 85% to about 95% by weight of the oil phase. The emulsifier component, which is soluble in the oil phase and suitable for forming a stable water-in-oil emulsion may be included in the oil phase in an amount of from about 1% to about 20% by weight of the oil phase. The emulsion may be formed at an emulsification temperature of from about 20° C. to about 130° C. and in certain examples from about 50° C. to about 100° C.

In general, the monomers may be included in an amount of about 20% to about 97% by weight of the oil phase and may include at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also include from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type include monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer (e.g. with water miscibility below 1 percent by weight monomer vs. water) may be added to the oil phase in weight percentages of from about 0% to about 15% by weight of the oil phase, in certain examples from about 2% to about 8%, to modify properties of the HIPE foams. In certain cases, "toughening" monomers may be desired to impart toughness to the resulting HIPE foam. These include monomers such as styrene, vinyl chloride, vinylidene chloride, isoprene, and chloroprene. Without intending to be bound by theory, it is believed that such monomers aid in stabilizing the HIPE during polymerization (also known as "curing") to provide a more homogeneous and better-formed HIPE foam which results in greater toughness, tensile strength, abrasion resistance, and the like. Monomers may also be added to confer flame retardancy, as disclosed, for example, in U.S. Pat. No. 6,160,028. Monomers may be added to impart color (for example vinyl ferrocene); to impart fluorescent properties; to impart radiation resistance; to impart opacity to radiation (for example lead tetraacrylate); to disperse charge; to reflect incident infrared light; to absorb radio waves; to make surfaces of the HIPE foam struts or cell walls wettable; or for any other desired property in a HIPE foam. In some cases, these additional monomers may slow the overall process of conversion of HIPE to HIPE foam, the tradeoff being necessary if the desired property is to be conferred. Thus, such monomers can also be used to slow down the polymerization rate of a HIPE. Examples of monomers of this type include styrene and vinyl chloride.

The oil phase may further include an emulsifier to stabilize the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol isostearate, and polyglycerol monomyristate (PGMM); (b) polyglycerol monoesters of -branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they constitute about 1% to about 20%, in certain examples about 2% to about 15%, and in certain other examples about 3% to about 12%, of the weight of the oil phase. In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Any photoinitiators included may be included at between about 0.05% and about 10%, and in some examples between about 0.2% and about 10% by weight of the oil phase. Lower amounts of photoinitiator allow light to better penetrate the HIPE foam, which can provide for polymerization deeper into the HIPE foam. However, if polymerization is performed in an oxygen-containing environment, it may be desired that there be enough photoinitiator present to initiate the polymerization and overcome oxygen inhibition. Photoinitiators can respond rapidly and efficiently to a light source with the production of radicals, cations, and other species that are capable of initiating a polymerization reaction. Photoinitiators selected for use in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl)phenyl]propanone] (sold by Lamberti spa, Gallarate, Italy as ESACURE® KIP EM.

The dispersed aqueous phase of a HIPE includes water, and may also include one or more components, such as initiator, photoinitiator, or electrolyte, wherein in certain examples, the one or more components are at least partially water soluble.

One component included in the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be included in the aqueous phase is a water-soluble free-radical initiator. The initiator can be present at up to about 20 mole percent based on the total moles of polymerizable monomers present in the oil phase. In certain examples, the initiator may be included in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, azo initiators, redox couples like persulfate-bisulfite, persulfate-ascorbic acid, and other suitable redox initiators.

Photoinitiator, if included in the aqueous phase, may be at least partially water soluble, and may constitute between about 0.05% and about 10%, and in certain examples between about 0.2% and about 10%, by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. Photoinitiators selected for use to form foams within contemplation of the present disclosure may absorb UV light at wavelengths of from about 200 nanometers (nm) to about 800 nm, in certain examples from about 200 nm to about 350 nm, and in certain examples from about 350 nm to about 450 nm. If a photoinitiator is to be included in the aqueous phase, suitable types of water-soluble photoinitiators may include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, zinc oxide, carbon black, or calcium carbonate; fibers; chain transfer agents; odor absorbers, for example activated carbon particulates; dissolved polymers; dissolved oligomers; and the like.

HIPE foam is produced from the polymerization of monomers included in the continuous oil phase of a HIPE. In certain examples, a HIPE foam layer may have one or more sublayers, and may be either homogeneous or heterogeneous polymeric open-celled foams. Homogeneity and heterogeneity relate to distinct layers within the same HIPE foam, which are similar in the case of homogeneous HIPE foams and differ in the case of heterogeneous HIPE foams. A heterogeneous HIPE foam may contain at least two distinct sublayers that differ with regard to their chemical composition, physical properties, or both; for example, sublayers may differ with regard to one or more of foam density, polymer composition, specific surface area, or cell size (also referred to as pore size). For example, for a HIPE foam if the difference relates to cell size, the average cell size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cm$^3$, another layer may have a density of at least about 0.024 g/cm3 or less than about 0.016 g/cm3, in certain examples at least about 0.027 g/cm$^3$ or less than about 0.013 g/cm$^3$, and in still other examples at least about 0.030 g/cm$^3$ or less than about 0.010 g/cm$^3$. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation (in its oil phase monomer precursor formulation), another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam layer may include first and second foam sublayers, wherein the first foam sublayer has a relatively larger pore or cell size, and the second sublayer has a relatively smaller pore or cell size. In a more particular example, when the HIPE foam layer is used to form an absorbent layer of a feminine hygiene pad, the first foam sublayer having relatively larger cell sizes may be layered over the second foam sublayer having relatively smaller cell sizes. The overlying first sublayer, having larger pores, can more rapidly accept, temporarily hold, and distribute deposits of fluid. The underlying second foam sublayer, having a greater number of smaller-sized pores per unit foam volume, will exhibit greater capillary fluid drawing capability, and draw the acquired fluid from the overlying first foam sublayer, restoring the first foam sublayer's ability to acquire more fluid from above. HIPE foam cell sizes may range from 1 to 200 μm and in certain examples may be less than 100 μm. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer.

The HIPE foam layers of the present disclosure are relatively open-celled. This refers to the individual cells or pores of the HIPE foam layer being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present disclosure, a HIPE foam is considered "open-celled" if at least about 80% of the cells in the HIPE foam that are at least 1 μm in size are in fluid communication with at least one adjoining cell.

In addition to being open-celled, in certain examples HIPE foams are adapted to be sufficiently hydrophilic to permit the HIPE foam to absorb aqueous fluids. In some examples the internal surfaces of a HIPE foam may be rendered hydrophilic by residual hydrophilizing surfactants or salts left in the HIPE foam following polymerization, or by selected post-polymerization HIPE foam treatment procedures such as those as described in references cited herein.

In certain examples, for example when it is used to form an absorbent layer of a feminine hygiene pad, a HIPE foam layer may be flexible and exhibit an appropriate glass transition temperature (Tg). The Tg represents the midpoint of the transition between the glassy and rubbery states of the polymer. In general, HIPE foams that have a Tg that is higher than the temperature of use can be strong but will also be relatively rigid and potentially prone to fracture (brittle). In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions; in certain other examples Tg will be less than about 30° C. For HIPE foams used in applications wherein the use temperature is higher or lower than ambient temperature, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent layers and/or sublayers within contemplation of the present disclosure, and materials and methods for their manufacture, also include but are not necessarily limited to those foams, materials and methods described in U.S. Pat. Nos. 10,313,724; 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; and US 2011/0160689, which are incorporated herein by reference to the extent not inconsistent herewith.

HIPE Foam Absorbent Layer with Clay Additive

In addition to the materials and methods reflected in the material set forth and cited above, it has been discovered that nanoparticles of at least one type of clay may be successfully incorporated into in a HIPE foam structure, to potentially beneficial effect. Without intending to be bound by theory, it is believed that adding clay nanoparticles to a HIPE may add compressive strength and stiffness to the resulting foam structure.

Preparation of Clay Nanoplatelet Additive

In one example, large aspect ratio nanoplatelets of sodium fluorohectorite ($[Na_{0.5}][Li_{0.5}Mg_{2.5}][Si_4]O_{10}F_2$—a clay mineral) may be prepared. The resulting nanoplatelets are very thin (approximately 1 nm) but have large aspect ratios (within a range and order of magnitude centered around approximately 18,000, ratio of largest dimension to thickness). As prepared, the platelets are presented in an agglomerated, stacked condition. In order to separate them with minimal requirement for energy input, they may be delaminated by immersing them in deionized water (e.g., approximately 1 mg/mL) and agitating the combination to create a suspension of separated clay nanoplatelets. The separated large aspect ratio nanoplatelets may be broken up (reduced in aspect ratio) via application of ultrasound energy to the suspension. It will be appreciated that such platelet size reduction may be beneficial to providing clay nanoparticles of a size suitable for purposes herein.

Without intending to be bound by theory, it is believed that, for a clay additive to have the beneficial effects described herein, it is desirable that the clay nanoparticles be suspended in the oil phase of the HIPE emulsion prior to polymerization. However, clay minerals are naturally hydrophilic, and therefore, will ordinarily resist immersion and suspension in oil phase constituents, without substantial (costly) input of mechanical energy and/or other alternative steps.

The inventors have discovered that the clay nanoparticles may be subjected to surface treatment and further preparation that efficiently renders them organophilic and thereby amenable to being immersed, dispersed and suspended in the oil phase with relatively low mechanical energy input.

A quantity of oligomeric surface modifier may be synthesized according to the following procedure: 19.8 g of EHMA, dissolved in 150 mL of toluene, may be filtrated over a basic alumina ($Al_2O_3$) (e.g., Sigma-Aldrich activated basic #199443, available from MilliporeSigma, St. Louis, MO) to remove the inhibitor, and then added together with 0.33 g AIBN to a solution of 1.5 g cysteamine in 200 mL of toluene. The mixture may be purged with nitrogen for 15 min. Then a reaction may be initiated by increasing the temperature to 85° C. for two hours. For purification, the organic phase may be extracted three times with water and then dried over magnesium sulfate. To protonate the oligomer, HCl in ethanol may be added in excess (16.2 mL, 1.25 M) before removing the solvent. A 1H-NMR spectrum of the product may be recorded to determine the chain length by comparing the signals of the methylene groups neighboring to sulfur and nitrogen with the signal of the methylene groups next to the oxygen. An average chain length of n≈5 resulted, which is in accordance with the applied ratio of monomer to cysteamine (5:1). A suitable oligomeric surface modifier, ammonium-terminated oligomeric poly(2-ethylhexyl methacrylate), results. (Hereinafter such surface modifier will be designated "oligomeric PEHMA-$NH_3^+$".)

To organophilize the clay nanoparticles, a solution of the oligomeric PEHMA-$NH_3^+$ in an organic liquid such as tetrahydrofuran (THF) solvent (e.g., approximately 40 mg/mL) may be prepared and added to the aqueous clay nanoparticle suspension prepared as described above, and stirred vigorously. The surface modifier will attach to the clay nanoparticles. Water may then be removed from the resulting suspension of organophilized clay nanoparticles by, e.g., centrifuging, and additional organic liquid such as THF may be added back to adjust the concentration of clay in liquid suspension, yielding a suspension of clay nanoparticles in THF or other organic liquid. Because the organic liquid used will be miscible with components of the contemplated oil phase blend, the suspension can be blended with the oil phase components, thereby immersing and dispersing the clay nanoplatelets throughout the oil phase blend.

It is believed that the process described above may save time, energy and/or material cost involved in providing or obtaining surface-modified clay nanoplatelets for incorporation into an oil phase component blend. It is also believed that the surface modifier described above is more effective for promoting immersion and dispersion of clay nanoparticles in a blend of oil phase components such as those contemplated herein.

Oil Phase and Aqueous Phase Examples

To prepare a HIPE foam within contemplation of the present disclosure, an oil phase blend may be prepared and include, for example, a majority weight percent fraction of (meth)acrylate(s) (monomer component); a minority weight percent fraction of cross-linker(s); and less than 15 weight percent, more preferably less than 10 weight percent emulsifier(s). In a particular example, the monomer(s) may be included at from 50 to 85 weight percent; the cross-linker(s) may be included at from 10 to 40 percent, the emulsifier(s) may be included at no greater than 15 weight percent, more preferably no greater than 10 weight percent.

One component included in the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Combining Emulsion Components

To avoid agglomeration and re-stacking of the organophilized clay nanoparticles, they may be kept in the THF/clay suspension prepared as described above. Following preparation of the oil phase blend, the THF/clay suspension may be added to the oil phase blend in an amount sufficient to add the desired weight percentage of clay nanoparticles to the oil phase (following expected removal of the THF). In some examples, the clay suspension may be added in an amount sufficient to bring its weight fraction of the oil phase blend to from 0.1 percent to 10 percent. After blending of the THF/clay suspension into the oil phase component blend, the THF may be removed via solvent evaporation or other separation means. The remaining suspension of clay nanoparticles in the oil phase blend may be further agitated e.g. via ultrasonication bath, to improve dispersion of the clay nanoparticles within the oil phase blend.

Most clay particle/organic liquid suspensions are unstable at relatively lower loadings of clay platelets, only reaching stability at loadings of 10-20% by weight clay in organic liquid—via interconnected networks of clay particles coming to rest in contact with each other in random orientations. Such networks can form following sufficient agitation. Without intending to be bound by theory, it is believed that the steps described above provide for a stable suspension of organophilized clay nanoparticles in the oil phase component blend contemplated herein, in which clay particles are less likely to agglomerate and settle out—at loadings of clay in combined oil phase components that are under 10% by weight clay, e.g., 0.1% up to 10% (ratio of [(clay+surface modifier)/oil phase blend]×100%). A stable suspension of the clay nanoparticles in the oil phase component blend provides for more flexibility in downstream handling and processing, since the manufacturer will be under less time pressure to use the suspension before clay nanoparticles begin to agglomerate and settle.

Following preparation of the oil phase blend with added, organophilized clay nanoparticles as described above, the oil phase blend may be combined with the aqueous phase solution (suitably pre-heated to, e.g., about 70 C) to a desired water-to-oil ratio, of an amount sufficient to create a HIPE. At this point the initiator solution may be added. The combination may be mechanically agitated to an extent desired to create a water-in-oil HIPE, having discontinuous phase aqueous phase droplets of a size reflective of the cell size desired in the foam end product. Following suitable agitation to create a HIPE of the desired droplet size, the emulsion may be held at a temperature (e.g., about 70 C) that promotes polymerization of the continuous phase, for a time sufficient to allow polymerization to occur.

As polymerization proceeds, the continuous phase reduces in volume (shrinks) about the aqueous phase droplets. Because the aqueous phase droplets are not compressible, as shrinkage occurs with polymerization, windows open in the walls formed of polymerized continuous phase components, that previously separated the droplets. The resulting foam structure of polymerized continuous phase components will have the form of a network of interconnected struts defining open (windowed) cells, occupied by the aqueous phase. The structure may then be washed or flushed as desired and then dewatered as described above, to yield an open-cell foam. The clay nanoparticles will be at least partially captured within the polymeric material forming the struts.

Without intending to be bound by theory, it is believed that the clay nanoparticles added to the oil phase in the manner described above have the effect of creating a more useful HIPE foam because it minimizes formation of agglomerations of clay particles which may otherwise negatively affect mechanical properties of the foam. It may also improve the consistency of aqueous phase droplet sizes, and thereby, improve the consistency of cell sizes, window sizes and strut structure within the resultant foam. The foam is imparted with improved compression modulus and compression strength as a result. Further, without intending to be bound by theory, it is believed that the presence of the clay in the foam may increase hydrophilicity of the foam struts/cell walls, and thereby, may improve the ability of the foam to draw in, wick and absorb aqueous fluid.

Further details concerning preparation of HIPE foams with clay nanoparticle additives as described herein may be found in L. Mayr, A. Simonyan, J. Breu and M. Wingert, *Structural and Mechanical Impact of Synthetic Clay in Composite Foams Made via High Internal Phase Emulsions*, Polymer Composites, Vol. 42, Issue 1, pp. 353-361 (January 2021) which is incorporated herein by reference. The cited Mayr et al. paper describes experiments in which HIPE foams were made with and without added clay nanoparticles, for structural examination by SEM and mechanical evaluation, in order to demonstrate the effects of the addition of the clay.

The following examples further illustrate effects of the surface modifier(s) described herein, upon the stability of a suspension of clay nanoparticles in an organic liquid blend that might be included as the oil phase component of a HIPE.

Example 1

Samples of three differing suspensions of clay nanoparticles in oil phase blends, poured into three respective vials, were visually evaluated for clay sedimentation (settling) at room temperature (21° C.). All three vials were created containing clay suspensions in an oil. The base oil phase blend (prior to addition of clay) consisted of a mixture of three monomers and two emulsifiers. A mixture of 38% 2-ethylhexyl methacrylate, 37% 2-ethylhexyl acrylate, 17.6% ethylene glycol dimethacrylate, 6.5% PGS and 0.9% DTDMAMS were stirred until the emulsifiers are completely dissolved.

The first vial contained 1 weight percent HecPEHMA and 99 weight percent oil phase. Here, clay, specifically $Na_{0.5}$-fluorohectorite $[Na_{0.5}][Li_{0.5}Mg_{2.5}][Si_4]O_{10}F_2$ ("NaHec") was obtained by melt synthesis as described by Stöter, M.; Kunz, D. A.; Schmidt, M.; Hirsemann, D.; Kalo, H.; Putz, B.; Senker, J.; Breu, J., *Nanoplatelets of sodium hectorite showing aspect ratios of approximately 20,000 and superior purity*, Langmuir 2013, 29, 1280-1285. Upon immersion in water, the NaHec spontaneously delaminates into single 1 nm thick nanoplatelets retaining their original largest dimensions (~20 μm) with an average aspect ratio of ~20,000. Sufficient water was added to create a clay concentration of 1 mg/mL aqueous suspension.

An oligomer, PEHMA, was synthesized according to a method described by Wu, T.; Liu, A.; Xie, T.; Yang, G., *Evaluation of ammonium terminated PMMA as compatibilizers for monomer casting polyamide6/clay nanocomposites*, Journal of Polymer Science Part B: Polymer Physics 2008, 46 (17), 1802-1810. 19.8 g of EHMA, dissolved in 150 mL of toluene, were filtrated over a basic alumina ($Al_2O_3$) (e.g., Sigma-Aldrich activated basic #199443, available from MilliporeSigma, St. Louis, MO) to remove the inhibitor and then added together with 0.33 g AIBN to a solution of 1.5 g cysteamine in 200 mL of toluene. The mixture was purged with nitrogen for 15 min. The reaction was then initiated by increasing the temperature to 85° C. for two hours. For purification, the organic phase is extracted three times with water and then dried over magnesium sulfate. To protonate the oligomer, HCl in ethanol was added in excess (16.2 mL, 1.25 M) before removing the solvent. The $^1$H-NMR spectrum of the product was recorded to determine the chain length by comparing the signals of the methylene groups neighboring to sulfur and nitrogen with the signal of the methylene groups next to the oxygen. An average chain length of n≈5 resulted, which is in accordance with the applied ratio of monomer to cysteamine (5:1).

Next, the resulting oligomeric surface modifier was used to render the surfaces of the NaHec nanoplatelets organophilic. A solution of the modifier in THF (20 mL, 40 mg/mL) was added to the aqueous NaHec platelet suspension (500 mL, 1 mg NaHec per mL aqueous solution) under vigorous stirring. The suspension of the resulting clay nanoplatelets ("HecPEHMA") was centrifuged (15 min, 10,000 rpm) and the supernatant was discarded. The bottom/sediment from the centrifuge was then suspended in THF solvent at a concentration of 6 mg HecPEHMA per mL THF solution.

Finally, HecPEHMA in THF was added to the oil phase and THF was removed by evaporation, to an extent sufficient to obtain a concentration of 1 weight percent suspended HecPEHMA, in the oil phase). The suspension was ultrasonicated in an ultrasonication bath for 30 seconds to improve dispersion quality prior to filling the vial and evaluating its stability.

The second vial contained 1 weight percent Sigma-Aldrich organophilized Montmorillonite ("O-MMT", which is obtained from the supplier as a relatively dry powder) and 99 weight percent oil phase. O-MMT containing 35-45 weight percent dimethyl dialkyl $C_{14}$-$C_{18}$ amine) was obtained from MilliporeSigma, St. Louis, MO 1 weight percent O-MMT was dispersed in the oil phase by vigorous shaking, followed by ultrasonication for 30 seconds.

The third vial contained 1 weight percent HecCTAB and 99 weight percent oil phase. Here, clay, specifically $Na_{0.5}$-fluorohectorite $[Na_{0.5}][Li_{0.5}Mg_{2.5}][Si_4]O_{10}F_2$ ("NaHec") was obtained by melt synthesis as described in literature by Stöter et al., supra. Upon immersing in water the NaHec spontaneously delaminates into single 1 nm thick nanoplatelets, retaining their original largest dimensions (~20 μm) having an average aspect ratio of ~20,000. Sufficient water was added to create a clay concentration of 2 mg/mL aqueous suspension. A solution of CTAB (cetyltrimethyl ammonium bromide) in water (3 mL, 20 mg/mL) was added to 50 mL of 2 mg/mL aqueous NaHec suspension under vigorous stirring. The suspension of organophilic hectorite (HecCTAB) was centrifuged (15 min, 10,000 rpm) and the supernatant was discarded. The bottom/sediment from the centrifuge was then suspended in THF solvent at a concentration of 8 mg HecCTAB per mL THF. The HecCTAB/THF suspension was added to the oil phase and THF was removed by evaporation, to an extent sufficient to obtain a concentration of 1 weight percent suspended HecCTAB, in the oil phase. The suspension was ultrasonicated in an ultrasonication bath for 30 seconds to improve dispersion quality.

Immediately after each of the three clay suspensions was removed from the ultrasonication bath, an unused, clean 4 mL glass vial was filled with approximately 3 mL of such clay suspension, and then photographs were taken of the vial, initially (approximately after 2 minutes) and also after different time increments as indicated in the Brief Description of the Drawings. Now referring to and comparing FIGS. 3A-3C, 4A-4C, 5A-5C and 6A-6C, it can be seen that FIG. 6A shows that the oil phase blend containing 1 weight percent HecPEHMA, 99% oil phase is stable at room temperature even after 1 week, meaning the HecPEHMA did not sediment/settle to the bottom of the vial. FIG. 4B shows that after 1 hour, the oil phase blend containing 1 weight percent O-MMT, 99% oil phase was mostly settled, containing more than 50% clear fluid on top of settled O-MMT clay particles. Finally, FIG. 4C shows that when a less preferred surface modifier is used (in this case, CTAB), after 1 hour the oil has settled, leaving about 40% clear oil phase on top of about 60% settled HecCTAB particles.

Example 2

Results observed in this example suggest that the surface modifier(s) and/or methods described herein may be effective for stabilizing a suspension of clay nanoparticles in an oil phase blend, even without the inclusion of emulsifiers (which are a type of surfactant) in the oil phase blend.

Once again, samples of three differing suspensions of clay nanoparticles in oil phase blends, poured into three respective vials, were visually evaluated for clay sedimentation (settling) at room temperature (21° C.). All three vials were created containing clay suspensions in an oil. The base oil phase blend (prior to addition of clay) consisted of a mixture of the three monomers as used in Example 1, but unlike Example 1, the oil phase blend contained no emulsifiers. A mixture of 40% 2-ethylhexyl methacrylate, 41% 2-ethylhexyl acrylate, and 19% ethylene glycol dimethacrylate were stirred until well blended.

The first vial contained a suspension of 1 weight percent HecPEHMA and 99 weight percent oil phase, with the emulsifiers omitted but otherwise prepared as described in Example 1.

The second vial contained a suspension of 1 weight percent Sigma-Aldrich organophilized Montmorillonite ("O-MMT", which is obtained from the supplier as a relatively dry powder) and 99 weight percent oil phase, with the emulsifiers omitted but otherwise prepared as described in Example 1.

The third vial contained a suspension of 1 weight percent HecCTAB and 99 weight percent oil phase, again, with the emulsifiers omitted but otherwise prepared as described in Example 1.

Immediately after each of the three clay suspensions was removed from the ultrasonication bath, an unused, clean 4 mL glass vial was filled with approximately 3 mL of such clay suspension, and then photographs were taken of the vial, initially (2 minutes after pouring) and also after 24 hours as indicated in the Brief Description of the Drawings. Now referring to and comparing FIGS. 7A-7C through 10A-10C, it can be seen in FIGS. 8A and 10A show that the oil phase blend containing 1 weight percent HecPEHMA, 99% oil phase is stable at room temperature even after 24 hours, meaning that the HecPEHMA did not sediment/settle to the bottom of the vial. FIGS. 8B and 10B show that after 24 hours, the vial containing 1 weight percent O-MMT, 99% oil phase was mostly settled, containing more than 50% clear fluid on top of settled O-MMT clay particles. Finally, FIGS. 8C and 10C show that when a less preferred surface modifier is used (in this case, CTAB), after 24 hours the oil phase blend has settled, leaving about 30% clear oil phase components on top of about 70% settled HecCTAB particles.

Example 3

Results observed in this example suggest that the clay surface modifier(s) and/or methods described herein may be effective for improving foam properties.

High internal phase emulsions were synthesized using a custom-made setup. The external oil phase was filled in a polypropylene bottle which is placed in a heated (65° C.) double jacketed beaker. The internal aqueous phase was pumped (25 mL/min) via a heating bath (70° C.) into the PP bottle. The initiator solution was directly added to the PP bottle at the beginning of the addition of the aqueous phase. Emulsification was assured by an overhead stirrer at 200 rpm. After complete addition of the aqueous phase, stirring continued for another 2 min. Curing of the foam occurred overnight in an oven set at 80° C. Afterwards, the wet foam was cut into 3 mm thick slices. These slices were washed with deionized water and dried afterwards.

Eight (8) grams of oil phase, including 65 wt. % 2-ethylhexyl acrylate, 28 wt. % ethylene glycol dimethacrylate, 6 wt. % polyglycerol isostearate and 1 wt. % DTDMAMS, was used. The aqueous phase included 152 g of a 2 wt. % sodium chloride solution and 8 g of a 4 wt.-% solution of sodium persulfate. The water-to-oil ratio was systematically varied in order to get different foam densities. The foam density was calculated by the mass and the dimensions of the specimens used for the compression tests. The relative density was determined by dividing the foam density by the bulk polymer density.

In addition, clay-containing foams were made following the same procedure, but adding clay into the oil phase prior to emulsification.

Surface modified clay (specifically, HecPEHMA) was prepared as described in Example 1, except that an aqueous delaminated hectorite suspension (4 mg/mL) was ultrasonicated for 15 min applying a Hielscher UIP1000hd, immediately prior to combining the hectorite suspension with the solution of PEHMA in THF. After preparation of HecPEHMA was complete, the bottom/sediment from the centrifuge was then suspended in THF solvent at a concentration of 6 mg HecPEHMA per mL THF solution. The desired amount (0.5-2 wt. % referred to oil phase) of organophilic hectorite in THF was mixed with the oil phase. Prior to emulsification, THF was removed by evaporation and the suspension was ultrasonicated in an ultrasonication bath for 30 seconds to improve dispersion.

Figure 11:
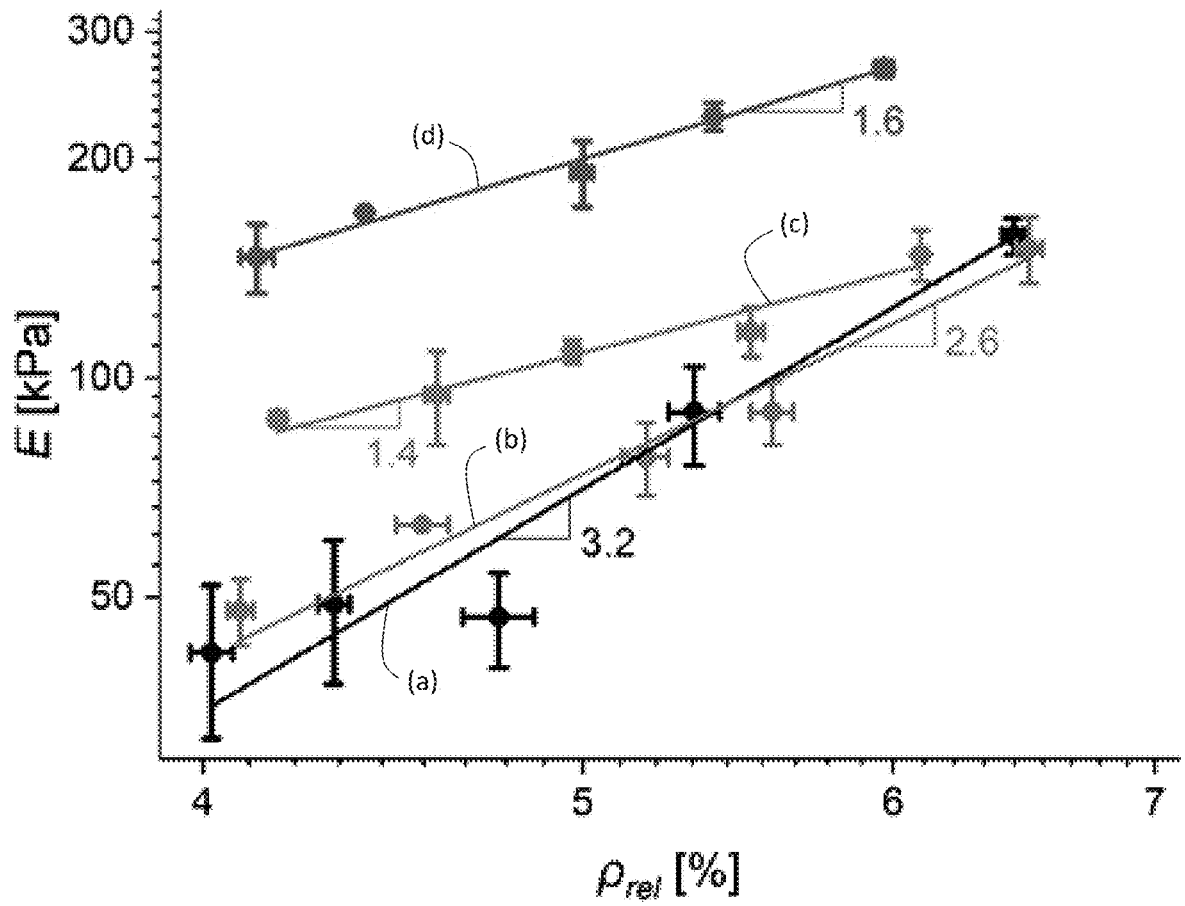
FIG. 11 depicts plots of compression moduli vs. foam densities, for various examples: (a) no filler; (b) 0.5 wt. % HecPEHMA; (c) 1 wt. % HecPEHMA; and (d) 2 wt. % HecPEHMA.

Compression tests were done at a Zwick Z050 universal testing machine (Zwick Roell, testXpert II) equipped with a 0.5 kN cell load. Cylindrical samples with a diameter of 25 mm and a height of 3 mm were cut from the washed and dried foams. All measurements were done at room temperature and a compression rate of 0.3 mm/min. The samples were compressed to 50% of the original height. Results in FIG. 11 reveal a substantial improvement to compressive modulus with the addition of the clay.

Figure 12:
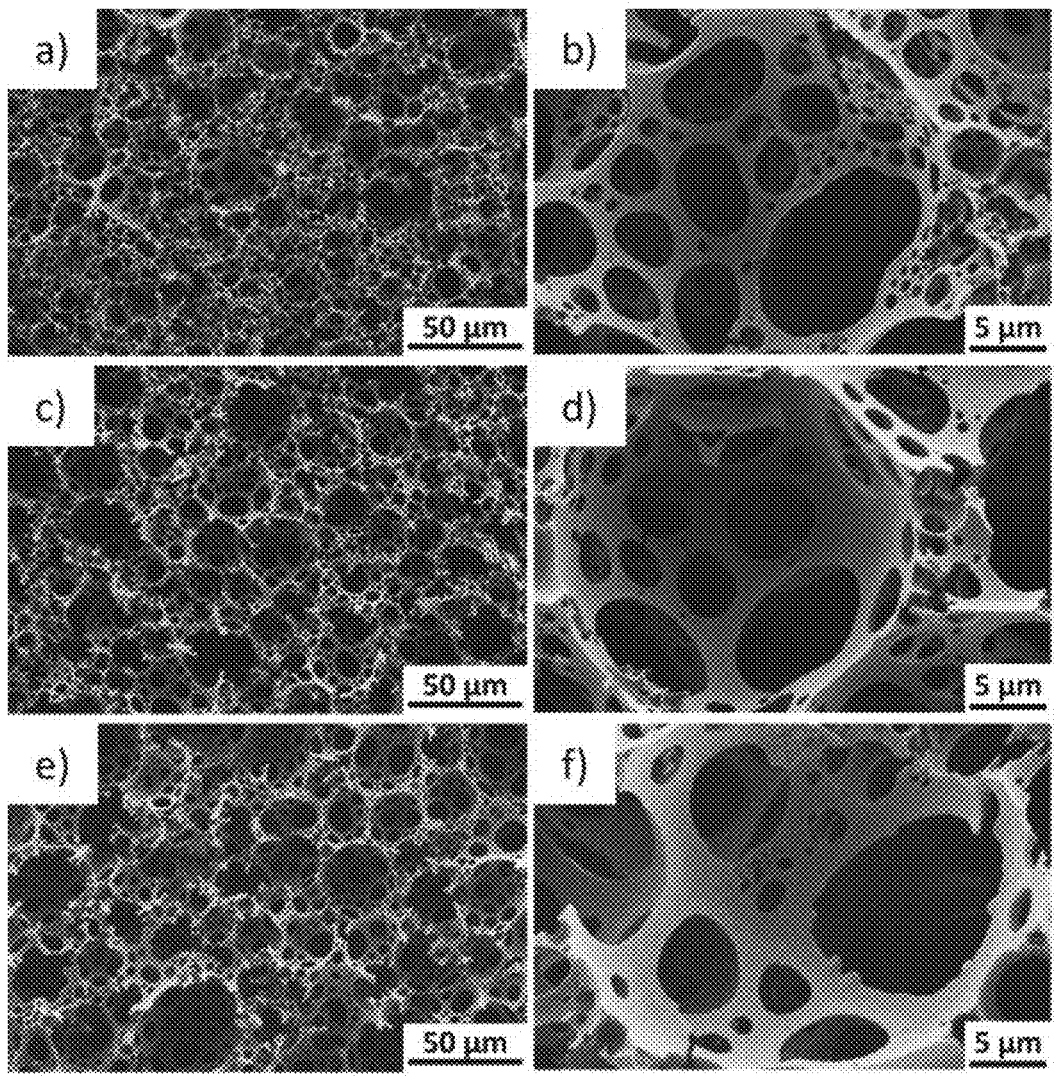
FIG. 12 is a group of SEM images, at magnifications reflected in the scale values at lower right corners of images, of 5% relative density foams with: no filler (images (a) and (b)); 1 wt. % HecPEHMA (images (c) and (d)); and 2 wt. % HecPEHMA (images (e) and (f)).

Because HecPEHMA was transferred from THF to the oil phase via solvent evaporation, the clay is never going through a dry state, which would inevitably trigger partial restacking of the clay platelets into band-like agglomerations and this is a benefit leading to a stiffer foam with HecPEHMA versus previously available forms of clay. This way suspensions in THF or the oil phase were obtained that were stable with no visually detectable sedimentation. With all applied HecPEHMA contents (0.5-2 wt.-% referred to the oil phase), the emulsions could be polymerized successfully. Scanning electron microscopy (SEM) images were taken with a Zeiss LEO 1530 (Carl Zeiss AG) using an acceleration voltage of 3 kV. Prior to measurement, samples were cut at room temperature with a razor blade and then coated with 2 nm platinum at a Cressington Sputter Coater 208HR (Cressington Scientific Instruments). All unfilled and HecPEHMA-containing foams had an interconnected, open-cell structure (see FIG. 12). No agglomerations of clay particles were observed in the SEM images.

As a point of comparison to the foams containing clays with custom-made organo-cation, commercial organophilic montmorillonite (O-MMT) was applied as a filler. As in Example 1, a desired amount of O-MMT (1 or 2 wt. % referred to oil phase) was dispersed in the oil phase by vigorous shaking, followed by ultrasonication for 30 seconds and the above procedure was repeated.

Figure 13:
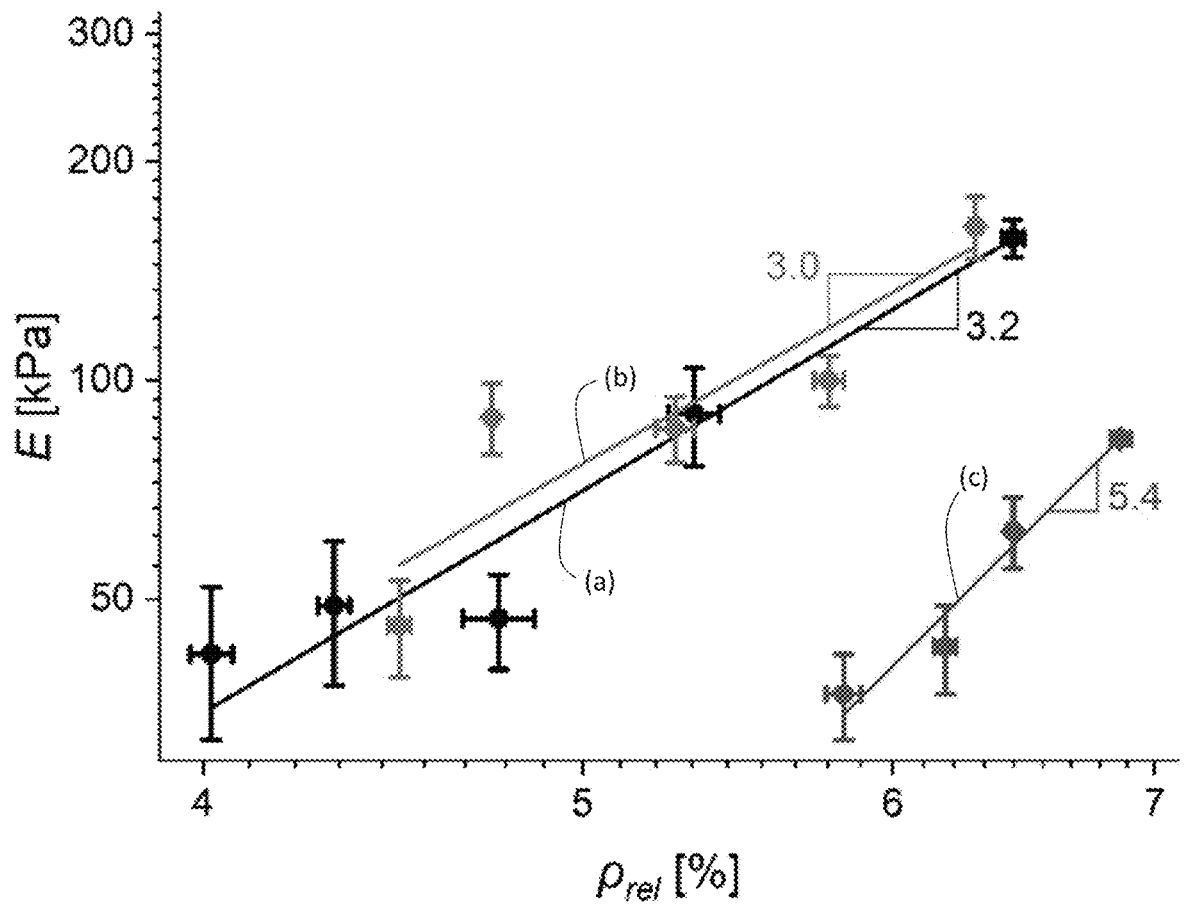
FIG. 13 depicts plots of compression moduli vs. foam densities, for various examples: (a) no filler; (b) 0.5 wt. % O-MMT; (c) 1 wt. % O-MMT; and (d) 2 wt. % O-MMT.

With a filler content of 1% O-MMT, all emulsions could be polymerized, leading to open-cell foams. With 2% O-MMT as filler, the lowest relative density foam condition resulted in a collapsed foam structure, believed to be so weak that it was either unable to bear its own weight and/or overcome attractive capillary forces. (Thus, data for this composition is not included in FIG. 13.) All other foams possessed a generally similar morphology versus the non-filled control. In contrast to the foams with 1% HecPEHMA, the foams with 1% O-MMT showed no increase in compression modulus (see FIG. 13; compare FIG. 11) versus neat foams. The foams with 2% O-MMT are substantially weaker than all other foams, including the neat foams (foams without added clay).

Use in Absorbent Layer

As reflected in FIG. 1, an absorbent layer formed of HIPE foam as described herein may include one or more patterns of perforations 42, including at least a first pattern disposed within an expected discharge location (coincidental and/or co-located with bonding region 25) overlying the intersection of longitudinal and lateral axes 100, 200 of the pad. Perforations 42 may be punched, cut or otherwise formed through the entire z-direction depth of the HIPE foam absorbent layer, or only through a wearer-facing layer or partially into the wearer-facing portion thereof. When a HIPE foam absorbent layer is disposed in direct contact with a topsheet as described herein, with no intervening acquisition layer formed of another material, perforations 42 may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such perforations help decrease bending stiffness of the absorbent layer, which may help increase comfort of the pad for the wearer. A pattern of perforations having an average radius or other largest dimension of 1.0 mm to 4.0 mm, and more preferably 1.5 mm to 3.5 mm may be included, within, for example, the area occupied by the bonding region 25. The pattern may include perforations at a numerical density of 3.0 to 9.0 perforations per $cm^2$, and more preferably 4.0 to 8.0 perforations per $cm^2$. In selecting the appropriate average size, numerical density, and surface area occupied by the pattern of perforations, the manufacturer may wish to balance the volume of the "reservoirs" desired with the need to retain absorbent material in locations proximate to and about the expected discharge location. Additional details concerning configurations of such perforations in combination with examples of suitable absorbent layers may be found in U.S. Pat. No. 8,211,078.

The absorbent layer formed of HIPE foam should be imparted with capability to effectively draw discharged fluid from a topsheet over a time of use/wear of the pad during menstruation that is normal and expected for feminine hygiene pads, for example, from 4 to 8 hours. Thus, it may be desired that an absorbent layer 40 formed of HIPE foam have a caliper (prior to wetting) that provides satisfactory fluid volume absorbency capacity for a standard-sized pad. Of course, a relatively thick pad can be manufactured, but that is typically deemed undesirable for daytime use in view of desires for flexibility/pliability and low bulk (low caliper), for comfort and discreetness under clothing. The manufacturer must balance these competing objectives. Accordingly a feminine hygiene pad with a HIPE foam absorbent layer as contemplated herein, it may be desired that the layer 40 have a caliper in the majority of its wearer-facing surface area (prior to wetting) of 1 mm to 5 mm, or more preferably 1.5 mm to 3.5 mm, or even more preferably 2.0 mm to 3.0 mm. (The caliper of a HIPE foam layer may be measured visually, with assistance of magnification/microscopy and/or photography or any other facilitating techniques and equipment, to any extent deemed useful.) Where the absorbent layer 40 includes two sublayers 40a, 40b as described herein, it may be desired that the upper sublayer 40a have a caliper (prior to wetting) of 0.64 mm to 3.2 mm, or preferably 0.96 mm to 2.24 mm, or even more preferably 1.28 mm to 1.92 mm; and it may be desired that the lower sublayer 40b have a caliper (prior to wetting) of 0.16 mm to 0.80 mm, or more preferably 0.24 mm to 0.56 mm, or even more preferably 0.32 mm to 0.48 mm.

Where a HIPE foam absorbent layer includes two or more sublayers 40a, 40b as described herein, clay nanoparticles may be included in only one, or fewer than all, of the sublayers present. This may be accomplished, for example, by adding/blending clay nanoparticles to/with, e.g., the oil phase components of only the particular HIPE emulsion that is the precursor of the foam sublayer in which inclusion of clay is desired. In a particular nonlimiting example in which a HIPE foam layer includes a first sublayer having a relatively larger average cell size, and a second sublayer having a relatively smaller average cell size, clay nanoparticles might be added to the HIPE emulsion that is the precursor of the first (larger-cell) sublayer. In another nonlimiting example, clay nanoparticles might be added to the HIPE emulsion that is the precursor of the second (smaller-cell) sublayer. In any case, the clay nanoparticles may be added to emulsion components as described above. In another nonlimiting example, clay nanoparticles of a first type may be included in a first sublayer, and clay nanoparticles of a second type may be included in a second sublayer. In another nonlimiting example, clay nanoparticles may have applied surface modifiers of respective first and second surface modifier types, added to first and second sublayers, respectively.

Backsheet

The backsheet 30 may be positioned adjacent an outward-facing surface of the absorbent layer 40 and may be joined thereto by any suitable attachment methods. For example, the backsheet 30 may be secured to the absorbent layer 40 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent layer 40 is not joined directly to the backsheet 30.

The backsheet 30 may be impervious, or substantially impervious, to liquids (e.g., urine, menstrual fluid) and may be manufactured from a thin plastic film, although other flexible liquid impervious materials may also be used. As used herein, the term "flexible" refers to materials which are compliant and will readily conform to the general shape and contours of the human body. The backsheet 30 may prevent, or at least substantially inhibit, fluids absorbed and contained within the absorbent layer 40 from escaping and reaching articles of the wearer's clothing which may contact the pad 10 such as underpants and outer clothing. However, in some instances, the backsheet 30 may be made and/or adapted to permit vapor to escape from the absorbent layer 40 (i.e., the backsheet is made to be breathable), while in other instances the backsheet 30 may be made so as not to permit vapors to escape (i.e., it is made to be non-breathable). Thus, the backsheet 30 may include a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523, 3,989,867, 3,156,242; WO 97/24097; U.S. Pat. Nos. 6,623,464; 6,664,439 and 6,436,508.

The backsheet may have two layers: a first layer including a vapor permeable aperture-formed film layer and a second layer including a breathable microporous film layer, as described in U.S. Pat. No. 6,462,251. Other suitable examples of dual or multi-layer breathable backsheets for use herein include those described in U.S. Pat. Nos. 3,881,489, 4,341,216, 4,713,068, 4,818,600; EP 203 821, EP 710 471; EP 710 472, and EP 0 793 952.

In view of the description above, the following non-limiting examples of structures, compositions and combinations thereof, and methods and combinations thereof, are contemplated herein:

1. An open-cell foam comprising a structure of interconnected struts formed of polymeric material and defining open cells, resulting from polymerization of a continuous phase of a high internal phase water-in-oil emulsion, the struts comprising the polymeric material with clay nanoparticles at least partially captured therewithin, wherein the clay nanoparticles are present in combination with a surface modifier.
2. The foam of example 1, wherein the clay nanoparticles comprise clay selected from the group consisting of hectorite, Laponite, Montmorillonite, saponite, vermiculite and kaolin, and combinations thereof; more preferably clay selected from the group consisting of montmorillonite, hectorite and Laponite, and combinations thereof.
3. The foam of example 2 wherein the clay nanoparticles comprise hectorite.
4. The foam of any of the preceding examples wherein clay nanoparticles together with the surface modifier are present in an amount from 0.1 weight percent to 10 weight percent of the structure, more preferably from 0.5 weigh percent to 4 weight percent of the structure, and even more preferably from 1 weight percent to 2 weight percent of the structure.
5. The foam of any of preceding examples wherein the surface modifier comprises a cation terminated acrylate oligomer and/or a cation terminated methacrylate oligomer.
6. The foam of example 5 wherein the surface modifier comprises ammonium-terminated oligomeric poly(2-ethylhexyl methacrylate).
7. The foam of any the preceding examples, wherein the polymerized continuous phase comprises polymerized acrylate and/or methacrylate.
8. The foam of any preceding examples where the foam contains a Sauter mean diameter cell size between 1 micron and 300 micrometers.
9. An absorbent article (10) comprising a liquid permeable topsheet (20), liquid impermeable backsheet (30), and an absorbent layer (40) disposed between the topsheet and the backsheet, wherein the absorbent layer comprises the foam of any of examples 1-8.
10. The absorbent article of example 9 wherein the absorbent article is a feminine hygiene pad.
11. The absorbent article of either of examples 9 or 10 wherein the absorbent layer (40) comprises a plurality of sublayers (40a, 40b), each sublayer comprising an open-cell foam comprising a structure of interconnected struts formed of polymeric material and defining open cells, resulting from polymerization of a continuous phase of a high internal phase water-in-oil emulsion, wherein only one, or fewer than all, sublayers of the plurality of sublayers, comprises the foam of any of examples 1-8.
12. The absorbent article of example 11 wherein the open-cell foam comprised by a first of the plurality of sublayers has an average cell size that is relatively larger than that of the open-cell foam comprised by a second of the plurality of sublayers; and the open-cell foam comprised by the second of the plurality of sublayers has an average cell size that is relatively smaller than that of the open-cell foam comprised by the first of the plurality of sublayers.
13. The absorbent article of example 12 wherein the first of the plurality of sublayers comprises the foam of any of examples 1-8.
14. The absorbent article of example 12 wherein the second of the plurality of sublayers comprises the foam of any of examples 1-8.
15. The absorbent article of any of examples 11-14 wherein the absorbent layer comprises only two of said sublayers, the respective open-cell foams of said two sublayers being disposed respectively superadjacent and subjacent to, and in direct contact with, each other.
16. A nanoparticle comprising a clay nanoparticle and a surface modifier disposed on a surface of the clay nanoparticle, the surface modifier comprising a cation terminated acrylate oligomer and/or a cation terminated methacrylate oligomer.
17. The nanoparticle of example 16 wherein the surface modifier comprises ammonium-terminated oligomeric poly(2-ethylhexyl methacrylate).
18. The nanoparticle of either of examples 16 or 17 wherein the clay nanoparticle comprises clay selected from the group consisting of hectorite, Laponite, Montmorillonite, saponite, vermiculite and kaolin, and combinations thereof; more preferably clay selected from the group consisting of montmorillonite, hectorite and Laponite, and combinations thereof.
19. The nanoparticle of example 18 wherein the clay nanoparticle comprises hectorite.
20. A method for manufacturing a relatively stable suspension of clay particles in an organic liquid, comprising the steps of:
    i) blending dry clay nanoparticles with a medium comprising predominantly water, to create an aqueous first suspension of the clay nanoparticles;
    ii) providing a first solution of an oligomeric surface modifier in an organic solvent, wherein the organic solvent is miscible in water;
    iii) blending the first solution with the first suspension, and thereby causing the oligomeric surface modifier to attach to surfaces of the suspended clay nanoparticles to render the surfaces organophilic, and thereby creating a second suspension of organophilized clay nanoparticles; and
    iv) removing a majority of the water from the second suspension to create a third suspension of organophilized nanoparticles.
21. The method of example 20 wherein the clay nanoparticles comprise clay selected from the group consisting of hectorite, Laponite, Montmorillonite, saponite, vermiculite and kaolin, and combinations thereof; more preferably clay selected from the group consisting of montmorillonite, hectorite and Laponite, and combinations thereof.
22. The method of example 21 wherein the clay nanoparticles comprise hectorite.
23. The method of any of examples 20-22 wherein the oligomeric surface modifier comprises a cation terminated acrylate oligomer and/or a cation terminated methacrylate oligomer.
24. The method of example 23 wherein the oligomeric surface modifier comprises oligomeric $PEHMA-NH_3^+$.
25. The method of any of examples 20-24 wherein the organic solvent comprises tetrahydrofuran (THF).
26. A method for manufacturing an open cell foam structure comprising a polymerized continuous phase of a high internal phase water-in-oil emulsion, the structure comprising clay nanoparticles, the method comprising the steps of:
    i) preparing the third suspension of organophilized nanoparticles according to any of examples 20-25;
    ii) providing an oil phase component blend of a water-in-oil HIPE, the blend comprising at least one monomer;

iii) providing an aqueous phase component solution of the water-in-oil HIPE;

iv) providing an initiator solution;

v) blending the third suspension with the oil phase component blend to create a fourth suspension of the organophilized clay nanoparticles in the oil phase component blend; vi) optionally, removing the organic solvent from the fourth suspension;

vii) blending the fourth suspension with the aqueous phase component solution and the initiator solution with sufficient mechanical energy to create a water-in-oil HIPE having a continuous phase comprising the fourth suspension; and viii) polymerizing monomer components of the oil phase component blend to create an open cell foam structure.

27. The method of example 26 wherein the monomer comprises an acrylate or methacrylate.

28. The method of example 27 wherein the monomer comprises 2-ethylhexyl acrylate.

29. The method of any of examples 26-28 wherein the oil phase component blend comprises a cross-linker.

30. The method of example 29 wherein the cross-linker comprises ethylene glycol dimethacrylate.

31. The method of any of examples 26-30 wherein the oil phase component blend comprises an emulsifier.

32. The method of example 31 wherein the emulsifier comprises polyglycerol isostearate.

33. The method of either of examples 31 or 32 wherein the oil phase component blend comprises DTDMAMS.

34. The method of any of examples 26-33 wherein the aqueous phase component solution comprises sodium chloride (NaCl).

35. The method of any of examples 26-34 wherein the initiator solution comprises sodium persulfate.

36. An absorbent article comprising a liquid permeable topsheet, liquid impermeable backsheet, and an absorbent layer disposed between the topsheet and the backsheet, wherein the absorbent layer comprises an open cell foam structure manufactured according to the method of any of examples 26-35.

37. The absorbent article of example 36 wherein the absorbent article is a feminine hygiene pad.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety to the extent not inconsistent herewith and unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

In view of the foregoing disclosure, the following claims reflect non-limiting combinations of elements, features and methods that are contemplated:

APPENDIX

Pre-publication draft of academic paper: L. Mayr, A. Simonyan, J. Breu and M. Wingert, *Structural and Mechanical Impact of Synthetic Clay in Composite Foams Made via High Internal Phase Emulsions* (publication pending).

What is claimed is:

1. An absorbent article comprising a liquid permeable topsheet, a liquid impermeable backsheet, and an absorbent layer disposed between the topsheet and the backsheet, wherein the absorbent layer comprises an open-cell foam, the open-cell foam comprising a structure of interconnected struts formed of polymeric material and defining open cells, resulting from polymerization of a continuous phase of a high internal phase water-in-oil emulsion where the oil contains an emulsifier, the struts comprising the polymeric material with clay nanoparticles at least partially captured therewithin, wherein the clay nanoparticles are rendered organophilic with a surface modifier, wherein the clay nanoparticles comprise nanoplatelets of sodium fluorohectorite, and wherein the surface modifier is an ammonium-terminated oligomeric poly(2-ethylhexyl methacrylate) having an average chain length of about 5, resulted from a reaction of oligomerization of 2-ethylhexyl methacrylate with cysteamine.

2. The absorbent article of claim 1 wherein the absorbent article is a feminine hygiene pad.

3. The absorbent article of claim 1 wherein the absorbent layer comprises a plurality of sublayers, each sublayer comprising an open-cell foam comprising a structure of interconnected struts formed of polymeric material and defining open cells, resulting from polymerization of a continuous phase of a high internal phase water-in-oil emulsion, wherein only one, or fewer than all, sublayers of the plurality of sublayers, comprises the open-cell foam.

4. The absorbent article of claim 3 wherein the open-cell foam comprised by a first of the plurality of sublayers has an average cell size that is relatively larger than that of the open-cell foam comprised by a second of the plurality of sublayers; and the open-cell foam comprised by a second of the plurality of sublayers has an average cell size that is relatively smaller than that of the open-cell foam comprised by the first of the plurality of sublayers.

5. The absorbent article of claim 4 wherein the first of the plurality of sublayers comprises the open-cell foam.

6. The absorbent article of claim 5 wherein the second of the plurality of sublayers comprises the open-cell foam.

7. The absorbent article of claim 3 wherein the absorbent layer comprises only two of said sublayers, the respective open-cell foams of said two sublayers being disposed respectively superadjacent and subjacent to, and in direct contact with, each other.

* * * * *